(12) United States Patent
Lindgren

(10) Patent No.: US 6,854,466 B2
(45) Date of Patent: Feb. 15, 2005

(54) METHOD FOR PRODUCING A HEARING PROTECTION CUP, AND TOOL USED FOR ITS PRODUCTION

(75) Inventor: Mats Lindgren, Vikmanshyttan (SE)

(73) Assignee: AB Kompositprodukter Vikmanshyttan, Vikmanshyttan (SE)

( * ) Notice: Subject to any disclaimer, the term of this patent is extended or adjusted under 35 U.S.C. 154(b) by 41 days.

(21) Appl. No.: 10/466,757

(22) PCT Filed: Jan. 31, 2002

(86) PCT No.: PCT/SE02/00171

§ 371 (c)(1),
(2), (4) Date: Jul. 21, 2003

(87) PCT Pub. No.: WO02/060365

PCT Pub. Date: Aug. 8, 2002

(65) Prior Publication Data

US 2004/0065332 A1 Apr. 8, 2004

(30) Foreign Application Priority Data

Feb. 1, 2001 (SE) .............................. 0100292

(51) Int. Cl.$^7$ ................................ A61F 11/00
(52) U.S. Cl. ....................... 128/864; 128/866; 128/898; 381/371; 2/209
(58) Field of Search ................................ 128/864, 865, 128/866, 867, 868, 887, 898; 381/370, 371, 372, 373, 374; 181/128, 129; D24/106; 2/208, 209, 423; 379/430

(56) References Cited

U.S. PATENT DOCUMENTS

| | | | | |
|---|---|---|---|---|
| 2,801,423 A | * | 8/1957 | Shaw et al. ................... | 2/209 |
| 3,016,054 A | * | 1/1962 | Rosenblatt ................... | 128/866 |
| 3,430,261 A | * | 3/1969 | Benner .......................... | 2/423 |
| 3,661,225 A | * | 5/1972 | Anderson .................... | 181/129 |
| 3,719,954 A | * | 3/1973 | Beguin .......................... | 2/209 |
| 3,944,018 A | * | 3/1976 | Satory .......................... | 181/129 |
| 4,069,512 A | * | 1/1978 | Palmaer ........................ | 2/209 |
| 4,104,743 A | * | 8/1978 | Bottger ........................ | 2/423 |
| 4,404,434 A | * | 9/1983 | Pelt et al. ................... | 381/370 |
| 4,517,418 A | * | 5/1985 | Baran et al. ................ | 381/374 |
| 4,944,361 A | * | 7/1990 | Lindgren et al. ........... | 181/129 |
| 6,353,938 B1 | * | 3/2002 | Young .......................... | 2/209 |
| 6,678,897 B2 | * | 1/2004 | Lindgren ...................... | 2/209 |

FOREIGN PATENT DOCUMENTS

| | | |
|---|---|---|
| BE | 393864 A | 1/1933 |
| FR | 2717735 A1 | 9/1995 |
| GB | 1249945 A | 10/1971 |

* cited by examiner

Primary Examiner—Fadi H. Dahbour
(74) Attorney, Agent, or Firm—Sughrue Mion, PLLC

(57) ABSTRACT

Tool for injection-molding a hearing protection cup which includes a curved shell with an opening for receiving an ear, and a washer which extends around the opening and is connected to the edge thereof. The washer projects inward across the opening along at least two opposite sides thereof and is intended to support a sealing and comfort ring which is intended to rest against the head. The tool includes a common mold cavity intended to produce the shell and the washer in one piece, and an insert which can be introduced into this mold cavity for forming the inner surfaces of the shell and of the washer. The insert is divided into at least three portions by means of dividing planes which extend in the same principal direction as the opposite sides of the opening. The invention also relates to a method for producing a hearing protection cup, and to a hearing protection cup produced using the method.

10 Claims, 3 Drawing Sheets

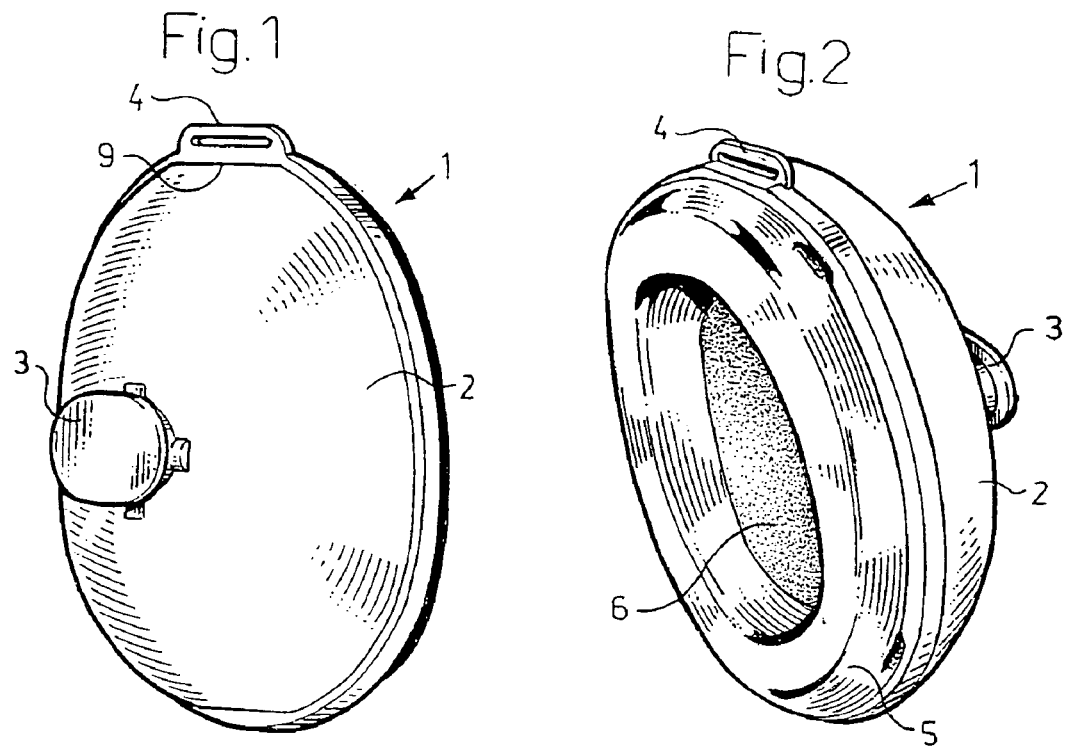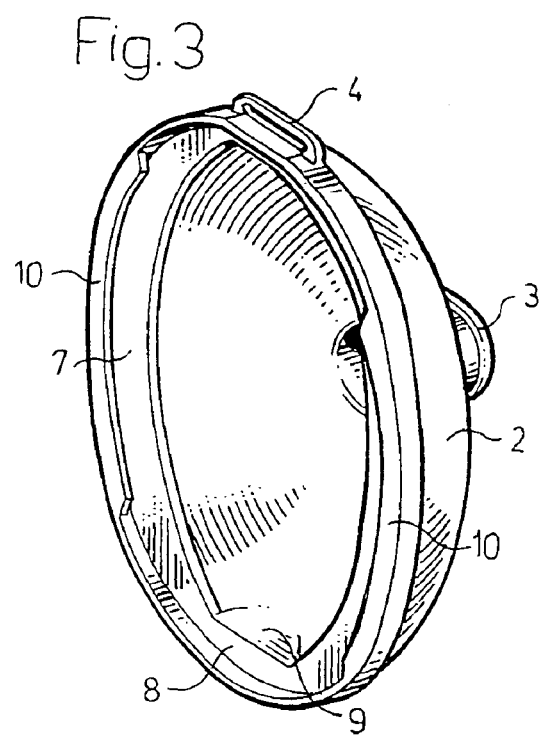

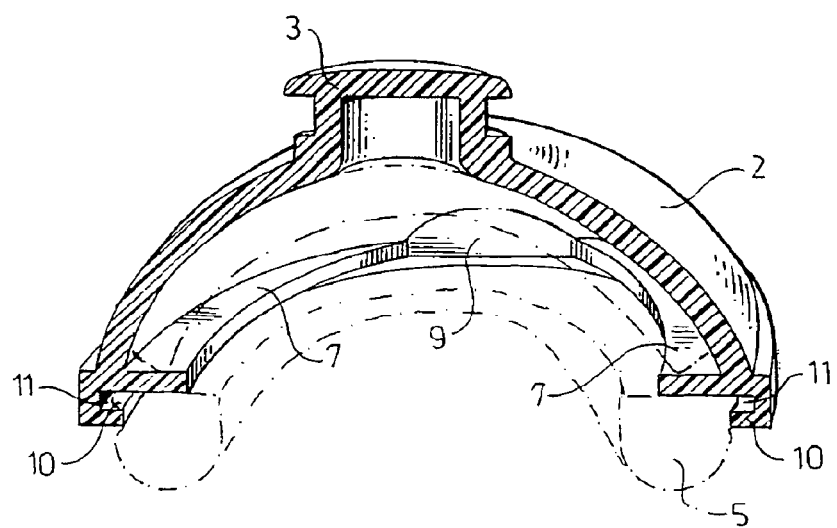
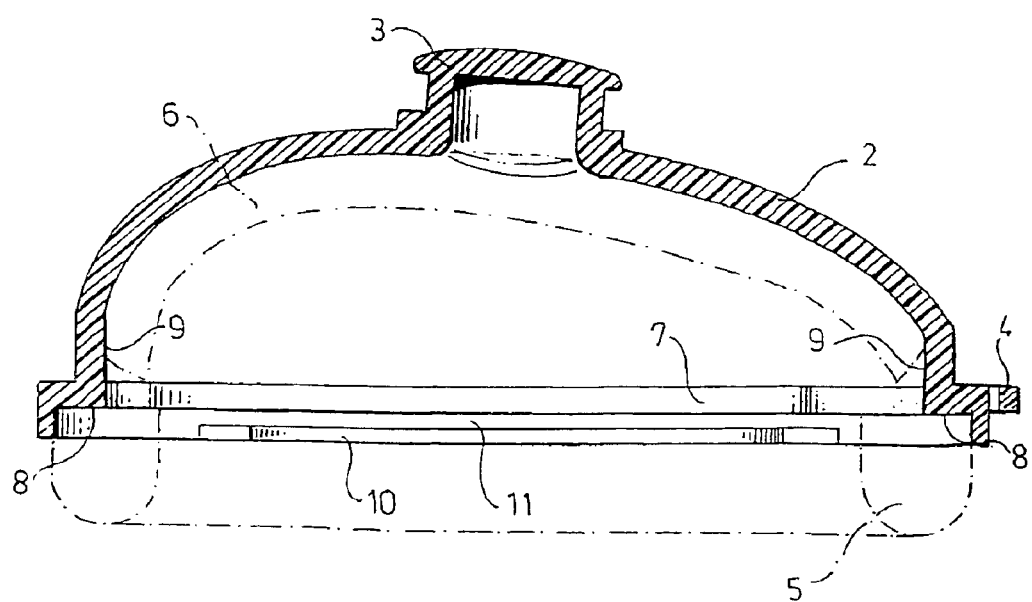

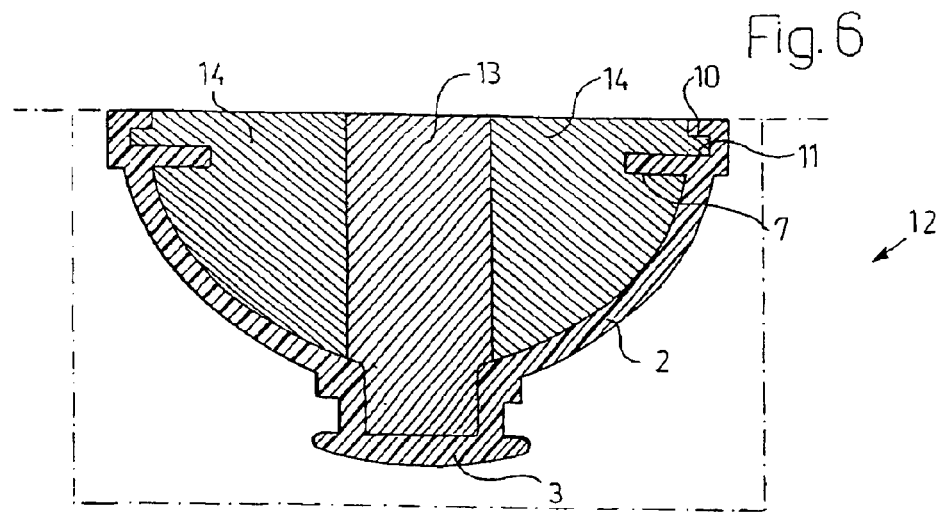
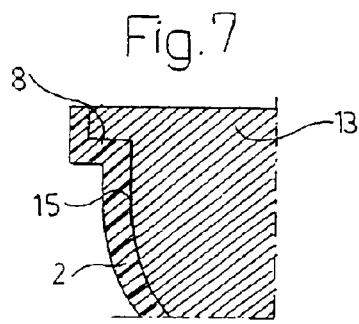
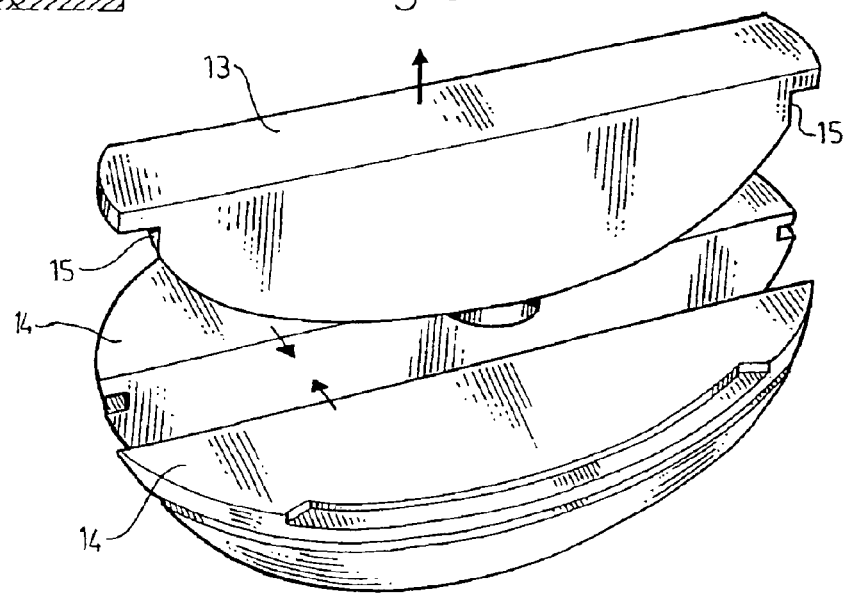

METHOD FOR PRODUCING A HEARING PROTECTION CUP, AND TOOL USED FOR ITS PRODUCTION

FIELD OF THE INVENTION

The present invention relates to a method for producing a hearing protection cup comprising a curved shell with an opening for receiving an ear and with a washer which extends around said opening, is connected to the edge thereof and projects inward across the opening along at least two opposite sides thereof, and which washer is intended to support a sealing and comfort ring which is intended to rest against the head.

The invention also relates to a tool for injection-molding a hearing protection cup by using this method.

BACKGROUND TO THE INVENTION

All product development is aimed in principle at reducing production costs and at achieving a higher-quality product. This applies to a very great extent to products of the hearing protection type. An analysis of the hearing protections currently available on the market shows that all the products follow certain common design solutions. It can be stated, for example, that all hearing protections of the cup type comprise two cups, each with a washer which extends around its opening and which is intended to support a sealing and comfort ring intended to rest against the head. The cups are either mounted in a frame or in separate holders intended to be fitted on a safety helmet.

Each cup and washer is produced by injection-molding of suitable plastic material in the form of two separate components, which are joined together in a later assembly step. They can be joined together in different ways, e.g. by adhesive bonding, ultrasound welding, or using snap-fit connections. The use of two production steps and a special assembly step results in higher production costs than would be the case if the production could take place in a single step, and it can result in a faulty product with poor fit between washer and cup, which can lead, for example, to sound getting through.

However, in a hearing protection cup of the abovementioned type, the washer intended for the sealing and comfort ring generally projects inward across the opening, from its edge formed by the shell of the cup. This means that the hollow space in the cup under the washer cannot be formed with a conventional insert since the latter, after a molding operation, cannot be removed again from the tool.

OBJECTS OF THE INVENTION

One object of the present invention is to make available a method for injection-molding of hearing protection cups in which the abovementioned problems are solved, so that it is possible to injection-mold a cup with an integrated washer in a single operation.

Another object is to make available a tool allowing a hearing protection cup with an integrated washer to be injection-molded in a single operation.

The invention is based on the realization that the above aims can be achieved by using a molding tool in which the insert which forms the inner surfaces of the hearing protection cup and of the washer is divisible. The shape of the cup is thus expediently modified so that the washer projects inward across the opening of the cup only along two opposite sides, while it projects outward from the outside of the shell along the remaining parts of the opening.

The special characteristic of a method of the type specified in the first paragraph is that the shell and washer of the cup are produced in one piece by injection-molding of a plastic material in a molding tool with an insert which is divided into at least three portions, the dividing planes between these portions extending in the same principal direction as said opposite sides of said opening.

This method considerably reduces the production costs, because fewer parts need to be produced and handled in the production process, and at the same time it eliminates the need for a separate step of joining together the cup and washer, which is often time-consuming. In addition, it eliminates any risk of sound getting through between washer and cup, as these are integrated into a single component.

It is preferable to use a three-part insert with a central portion and two side portions situated either side of the latter. After a molding operation, the central portion of the insert is first removed, after which the side portions are pushed in sequence or simultaneously into the hollow space after the central portion of the insert and are removed from the tool. Such a production method can be easily automated and results in reduced production costs.

The hearing protection cup preferably has a substantially oval opening, the washer projecting inward across the opening along part of the opposite long sides of the oval opening, while it projects outward from the outside of the shell along opposite end portions of the opening. The central portion of the three-part insert is used for forming the edge of the opening only along the opposite end portions of the opening where the washer does not project inward across the opening.

Other features of a production method according to the invention and of a tool for injection-molding a hearing protection cup are set out in the attached patent claims.

The invention will now be described in more detail below with reference to the embodiments shown by way of example in the attached drawings.

BRIEF DESCRIPTION OF THE FIGURES

FIGS. 1 and 2 are perspective views of a hearing protection cup according to the present invention.

FIG. 3 is a perspective view of the shell of a hearing protection cup according to FIGS. 1 and 2.

FIG. 4 shows a cross section through a hearing protection cup according to the invention.

FIG. 5 shows a longitudinal section through a hearing protection cup according to the invention.

FIG. 6 shows a cross section through a schematically depicted tool for injection-molding a hearing protection cup according to the invention.

FIG. 7 shows part of a longitudinal section through the tool according to FIG. 6.

FIG. 8 illustrates the design of a tool insert used in accordance with FIGS. 6 and 7.

DETAILED DESCRIPTION OF THE PREFERRED EMBODIMENT

The hearing protection cup 1 according to FIGS. 1 and 2 comprises a curved shell 2 of suitable plastic material with connection members 3, 4 to permit fitting on a crown frame or directly on a safety helmet. An elastic and soft sealing and comfort ring 5 is arranged on that side of the cup facing toward the head. Inside the cup shell 2 there is a sound-damping foamed plastic material 6.

The comfort ring 5 is supported by a washer 7, 8 (see FIG. 3) which is arranged around the oval opening of the cup and projects inward across the opening along opposite long sides of the cup, whereas it projects slightly outward from the curved shell of the cup 2 at its end portions in order to form a washer with a sufficient mounting surface around the whole opening. To obtain the outwardly projecting portions 8 at the ends of the cup, the shell of the cup 2 is modified so that it has a straight portion 9 at the short ends. The straight portions 9 adjoin the inner surface of the cup in such a way that there is no undercut at these end portions. The washer 7 projects inward across the opening along the remaining part of the opening of the cup.

Reference number 10 indicates two flanges which project inward across the washer 7, these flanges being used to fit the comfort ring 5 so that the latter is held securely on the cup 2, as is shown schematically in the cross section in FIG. 4. The comfort ring 5 is for this reason preferably provided with a stiffened base plate which can be driven into the groove 11 formed between the flanges 10 and the washer 7.

It will be seen from the longitudinal section in FIG. 5 that, at the straight end portions 9, the shell of the cup 2 does not have any undercut portion, for which reason these end surfaces can be formed with an insert which, after molding, can be easily removed from the inside of the cup. By contrast, the longitudinal edge portions of the cup with the washer 7 projecting inward across the opening cannot be formed with a one-piece insert.

According to the present invention, this problem is solved by using an insert which is divided in three in the longitudinal direction, as can be seen from the schematic cross section through a molding tool 12 in FIG. 6. The molding tool 12 comprises an outer mold and an insert which in the longitudinal direction is divided into a central portion 13 and two side portions 14 situated either side of the latter. The central portion 13 has a width which does not exceed the width of the straight portion 9 without undercut at the end portions of the cup. This central portion 13 of the insert with straight end portions 15 can be lifted straight up after a molding operation. This possibility can also be seen from FIG. 7 which is a part of a longitudinal section through one end portion of the insert 13 and shows that there is no undercut at the ends of the central portion 13.

Those parts of the washer 7 extending along the long sides of the shell of the cup 2 are in the form of flanges which are integrated with the shell. According to what has been stated above, these flanges and the other flanges 10 lying over them cannot be molded by means of an insert which is to be lifted straight up after a molding operation. For this reason, the side portions 14 of the insert are designed in such a way that, when the central portion 13 has been removed, they can be pushed together and thereafter lifted straight up (see FIG. 8). This is made possible by the fact that the engagement of the flanges 7 and 10 with the insert is released. If the engagement of the flanges 7 with the insert is very deep or the central portion 13 of the insert is very narrow, then, once the central portion 13 has been removed, it is alternatively possible for the one side portion 15 first to be pushed sideways and lifted up, and thereafter the second one.

By means of a modification of the technique described above, it is possible to produce cup shells in which the end portions are also designed with undercut portions. In this case the central portion 13 of the insert is designed with two transverse dividing planes, so that one can first remove the middle part of the central portion and then push its side parts together, after which these side parts can be removed. Thereafter, the side portions of the insert can then be removed, as has been described above.

The invention has been described above in connection with the design of a hearing protection cup shown in the drawings. However, the principle according to the invention can be used for producing cups or the like with other shapes which have undercut portions.

What is claimed is:

1. A method for producing a hearing protection cup which comprises a curved shell with an opening for receiving an ear, and a washer which extends around the opening and is connected to the edge thereof, and which washer projects inward across the opening along at least two opposite sides thereof and is intended to support a sealing and comfort ring which is intended to rest against the head, characterized in that the shell and the washer are produced in one piece by injection-molding of a plastic material in a molding tool with an insert which is divided into at least three portions, the dividing planes between these portions extending in the same principal direction as said opposite sides of said opening.

2. The method as claimed in claim 1, characterized in that a three-part insert is used which has a central portion and two side portions situated either side of the latter, and in that, after a molding operation, the central portion of the insert is first removed, after which the side portions are pushed in sequence or simultaneously into the hollow space after the central portion of the insert and are removed from the tool.

3. The method as claimed in claim 2 for producing a hearing protection cup with a substantially oval opening, and in which said washer projects inward across the opening along part of the opposite long sides of the oval opening, while it projects outward from the outside of the shell along the opposite end portions of the opening, characterized in that a three-part insert is used with a central portion which forms the edge of the opening only along said opposite end portions of the opening where the washer does not project inward across the opening.

4. The method as claimed in claim 1 for producing a hearing protection cup in which the washer extending around the opening projects inward across the opening along the entire periphery thereof, characterized in that a molding tool is used with an insert having three longitudinal dividing planes, and in which the central portion formed by these dividing planes is divided into three parts by means of two transverse dividing planes, and in that, after a molding operation, the middle part of the central portion is first removed, thereafter the side parts of the central portion, and finally the two side portions.

5. A tool for injection-molding a hearing protection cup which comprises a curved shell (2) with an opening for receiving an ear, and a washer (7, 8) which extends around the opening and is connected to the edge thereof, and which washer projects inward across the opening along at least two opposite sides thereof and is intended to support a sealing and comfort ring (5) which is intended to rest against the head, characterized in that it comprises a common molding cavity intended for producing the shell (2) and the washer (7, 8) in one piece, with an insert (13, 14) which is intended for forming the inner surfaces of the shell and of the washer and is divided into at least three portions, and in that the dividing planes of the insert extend in the same principal direction as said opposite sides of said opening.

6. The tool as claimed in claim 5, characterized in that the insert is in three parts and comprises a central portion and two side portions (14) situated either side of the latter, in that the central portion (13) of the insert can be separated from the side portions (14), so that, after a molding operation, the central portion of the insert can be removed first, after which the side portions can be pushed in sequence or simultaneously into the hollow space after the central portion of the insert and can be removed from the mold cavity.

7. The tool as claimed in claim 6 for producing a hearing protection cup with a substantially oval opening, and in which said washer (7, 8) projects inward across the opening along part of the opposite long sides of the oval opening, while it projects outward from the outside of the shell (2) along opposite end portions of the opening, characterized in that the central portion (13) of the three-part insert is intended to form the edge (9) of the opening only along said opposite end portions of the opening where the washer (8) does not project inward across the opening.

8. The tool as claimed in claim 7 for producing a hearing protection cup with a substantially oval opening, in which opposite end portions of the opening are substantially straight, characterized in that the central portion (13) of the insert has end portions (15) which are cut substantially straight.

9. The tool as claimed in claim 5 for injection-molding a hearing protection cup, in which said washer projects inward across the opening along the whole of its periphery, characterized in that the insert is designed with three longitudinal dividing planes, in that the central portion (13) formed by these dividing planes is divided into three parts by means of two transverse dividing planes, so that, after a molding operation, the middle part of the central portion can first be removed, thereafter the side parts of the central portion, and finally both side portions of the insert.

10. A hearing protection cup comprising a curved shell (2) with an opening for receiving an ear, and with a washer (7, 8) which extends around the opening and is connected to the edge thereof and is intended to support a sealing and comfort ring (5) intended to rest against the head, characterized in that the washer projects inward across the opening only along two opposite sides thereof, and in that the shell (2) and the washer (7, 8) are produced in one piece in a common injection-molding operation.

* * * * *